United States Patent
Wood (10) Patent No.: US 11,207,530 B2
(45) Date of Patent: Dec. 28, 2021

(54) RELATIVELY COMPACT IMPLANTABLE MEDICAL DEVICES AND ASSOCIATED METHODS FOR LOADING THE DEVICES INTO A DELIVERY CATHETER

(71) Applicant: Medtronic, Inc., Minneapolis, MN (US)

(72) Inventor: Rónán Wood, Co. na Gaillimhe (IE)

(73) Assignee: Medtronic, Inc., Minneapolis, MN (US)

( * ) Notice: Subject to any disclaimer, the term of this patent is extended or adjusted under 35 U.S.C. 154(b) by 683 days.

(21) Appl. No.: 14/612,855

(22) Filed: Feb. 3, 2015

(65) Prior Publication Data
US 2016/0220829 A1    Aug. 4, 2016

(51) Int. Cl.
*A61N 1/372*  (2006.01)
*A61N 1/362*  (2006.01)
*A61N 1/375*  (2006.01)

(52) U.S. Cl.
CPC ......... *A61N 1/37205* (2013.01); *A61N 1/362* (2013.01); *A61N 1/3756* (2013.01)

(58) Field of Classification Search
CPC .... A61N 1/3756; A61N 1/375; A61N 1/3752; A61N 1/3754; A61N 1/372; A61N 1/37205; A61N 1/362; A61N 1/057; A61N 1/0573; A61N 2001/0578; A61N 2001/058; A61B 17/221; A61B 17/3468; A61B 2017/22035; A61B 17/06004; A61B 2017/06009; A61B 2017/06014; A61B 2017/06019; A61B 2017/06023; A61B 2017/06042; A61B 2017/06047; A61M 25/0074; A61F 2/01; A61F 2/0044; A61F 2002/011; A61F 2002/016; A61F 2002/018; A61F 2002/0072
USPC ........................................................ 606/129
See application file for complete search history.

(56) References Cited

U.S. PATENT DOCUMENTS

| | | |
|---|---|---|
| 376,207 A | 1/1888 | Pavlik |
| 5,562,678 A | 10/1996 | Booker |
| 5,868,754 A | 2/1999 | Levine et al. |
| 8,364,280 B2 | 1/2013 | Marnfeldt et al. |
| 8,504,156 B2 | 8/2013 | Beilfuss et al. |
| 8,615,310 B2 | 12/2013 | Khairkhahan et al. |

(Continued)

OTHER PUBLICATIONS www.Wikipedia.org, "Tailhook",Feb. 2, 2015, 4 pages.

*Primary Examiner* — Katherine H Schwiker
(74) *Attorney, Agent, or Firm* — Shumaker & Sieffert, P.A.

(57) ABSTRACT

An implantable medical device includes an improved tether catch formed by a relatively rigid structure that has a hook surface extending between first and second ends thereof. The second end of the structure is spaced apart from another portion of the device by a gap of a size no greater than a thickness of a tether, for which the tether catch is formed to engage, when the tether is looped within a delivery catheter. The device may be loaded into the catheter by: positioning the looped portion of the tether in close proximity to the gap of the tether catch; creating tension in the positioned tether to bring the looped portion into a perimeter of the hooked surface; and then pulling the tether so that the looped portion thereof bears against the hooked surface, thereby bringing the device into engagement with a distal-most end of the delivery catheter.

8 Claims, 9 Drawing Sheets

(56) References Cited

U.S. PATENT DOCUMENTS

| | | | |
|---|---|---|---|
| 2006/0136070 A1* | 6/2006 | Pinchuk | A61B 17/00491 623/23.72 |
| 2008/0097482 A1* | 4/2008 | Bain | A61B 17/0469 606/144 |
| 2011/0270340 A1* | 11/2011 | Pellegrini | A61N 1/0573 607/9 |
| 2012/0197373 A1* | 8/2012 | Khairkhahan | A61N 1/3756 607/127 |
| 2012/0203246 A1* | 8/2012 | Staunton | A61N 1/0551 606/129 |
| 2013/0103047 A1* | 4/2013 | Steingisser | A61N 1/3756 606/129 |
| 2014/0058404 A1* | 2/2014 | Hammack | A61B 17/221 606/127 |
| 2014/0180306 A1 | 6/2014 | Grubac et al. | |
| 2014/0200462 A1 | 7/2014 | Stalker et al. | |
| 2014/0207149 A1 | 7/2014 | Hastings et al. | |
| 2014/0236220 A1* | 8/2014 | Inoue | A61F 2/01 606/200 |
| 2014/0257324 A1 | 9/2014 | Fain | |

* cited by examiner

RELATIVELY COMPACT IMPLANTABLE MEDICAL DEVICES AND ASSOCIATED METHODS FOR LOADING THE DEVICES INTO A DELIVERY CATHETER

FIELD OF THE DISCLOSURE

The present disclosure pertains to implantable medical devices, and more particularly to features thereof and associated methods for loading the devices into a delivery catheter.

BACKGROUND

Figure 1:
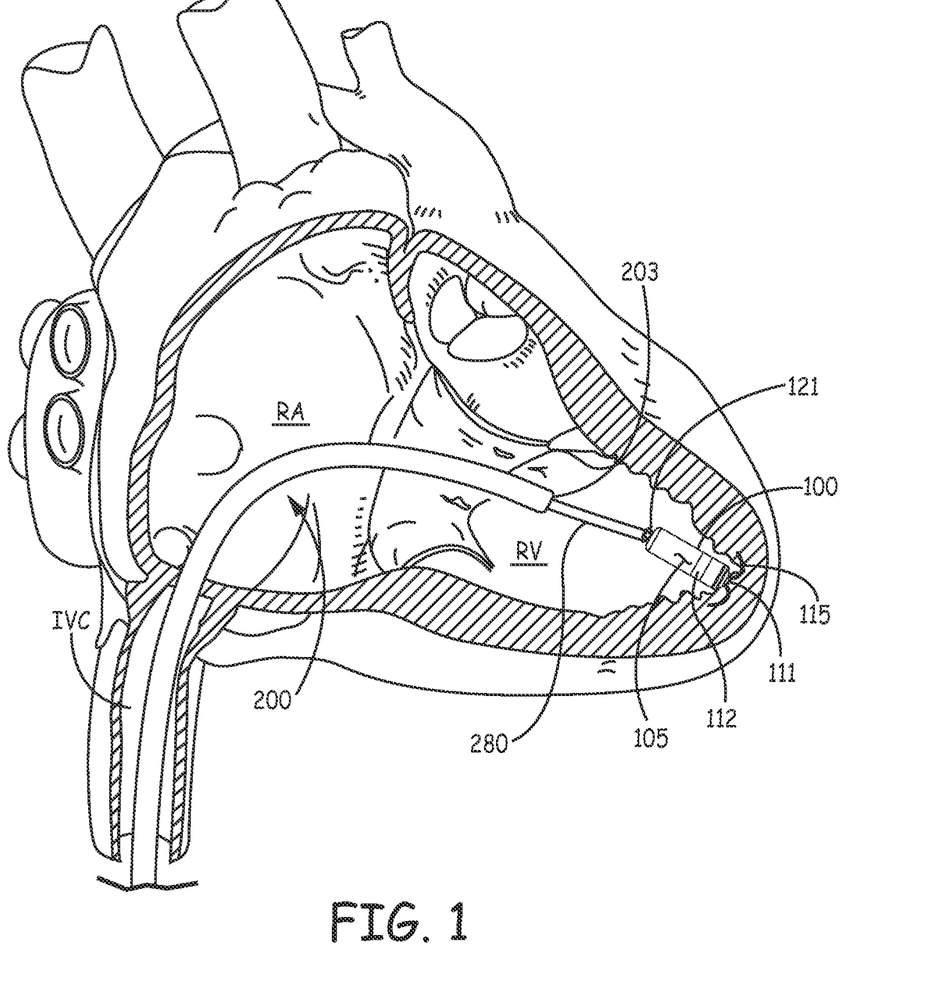
FIG. 1 is a schematic showing an example of an implanted medical device for cardiac stimulation.

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such a device 100 is illustrated, wherein an hermetically sealed enclosure 105, preferably formed from a biocompatible and biostable metal such as titanium, contains a pulse generator, or an electronic controller and associated power source (not shown), to which at least one electrode 111 is coupled, for example, by a hermetic feedthrough assembly (not shown) like those known to those skilled in the art of implantable medical devices. Enclosure 105 may be overlaid with an insulative layer, for example, medical grade polyurethane, parylene, or silicone, and a portion of the insulation layer may be removed to form another electrode 112, for example, to provide bipolar pacing and sensing in conjunction with electrode 111.

FIG. 1 illustrates device 100 having been deployed out from a distal portion of a delivery catheter 200, which has been maneuvered up through the inferior vena cava IVC and into the right ventricle RV from the right atrium RA. FIG. 1 further illustrates the deployed device 100 being fixed at an implant site by a fixation member 115 thereof, and an elongate tether 280, which extends within one or more lumens of delivery catheter 200, so that a looped portion thereof extends out from a distal opening 203 of catheter 200, being coupled to a tether catch 121 of device 100. A proximal portion of tether 280 (not shown), which extends out from a proximal end of delivery catheter 200, is accessible to an operator so that the operator may tug on tether 280 to test the fixation of device 100 at the implant site, and, if necessary, apply a greater force to tether 280 to remove device 100 from the implant site for repositioning at a more suitable site. But, if satisfied with the performance of device 100 at the illustrated implant site, the operator may release the looped tether 280 from engagement with tether catch 121, and withdraw tether 280 through delivery catheter 200.

Although various configurations of tether catches 121 for relatively compact medical devices, like device 100, are known in the art, for example, like the tether attachment structures disclosed in commonly assigned U.S. Pat. No. 8,504,156, there is still a need from improved tether catches that can increase the ease of loading such devices in delivery catheters.

SUMMARY

Implantable medical devices, according to embodiments disclosed herein, include an improved tether catch formed by a relatively rigid structure that has a hook surface extending between first and second ends thereof. In some embodiments, the structure protrudes from a proximal end of a housing of the device, the hook surface includes a portion facing directly toward the proximal end of the housing, and the second end of the structure is spaced apart from the proximal end by a gap of a size no greater than a thickness of a tether. According to some alternate embodiments, the structure protrudes from a free end of a flexible extension of the device, the hook surface includes a portion facing directly toward the free end of the flexible extension, and the second end of the structure is spaced apart from the free end by the aforementioned gap. In either case, the tether, for which the tether catch is formed to engage, is looped within a delivery catheter. According to some methods, the device may be loaded into the delivery catheter by: positioning the looped portion of the tether in close proximity to the gap of the tether catch; creating tension in the positioned tether to bring the looped portion into a perimeter of the hooked surface; and then pulling the tether so that the looped portion thereof bears against the hooked surface, thereby bringing the device into engagement with a distal-most end of the delivery catheter.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
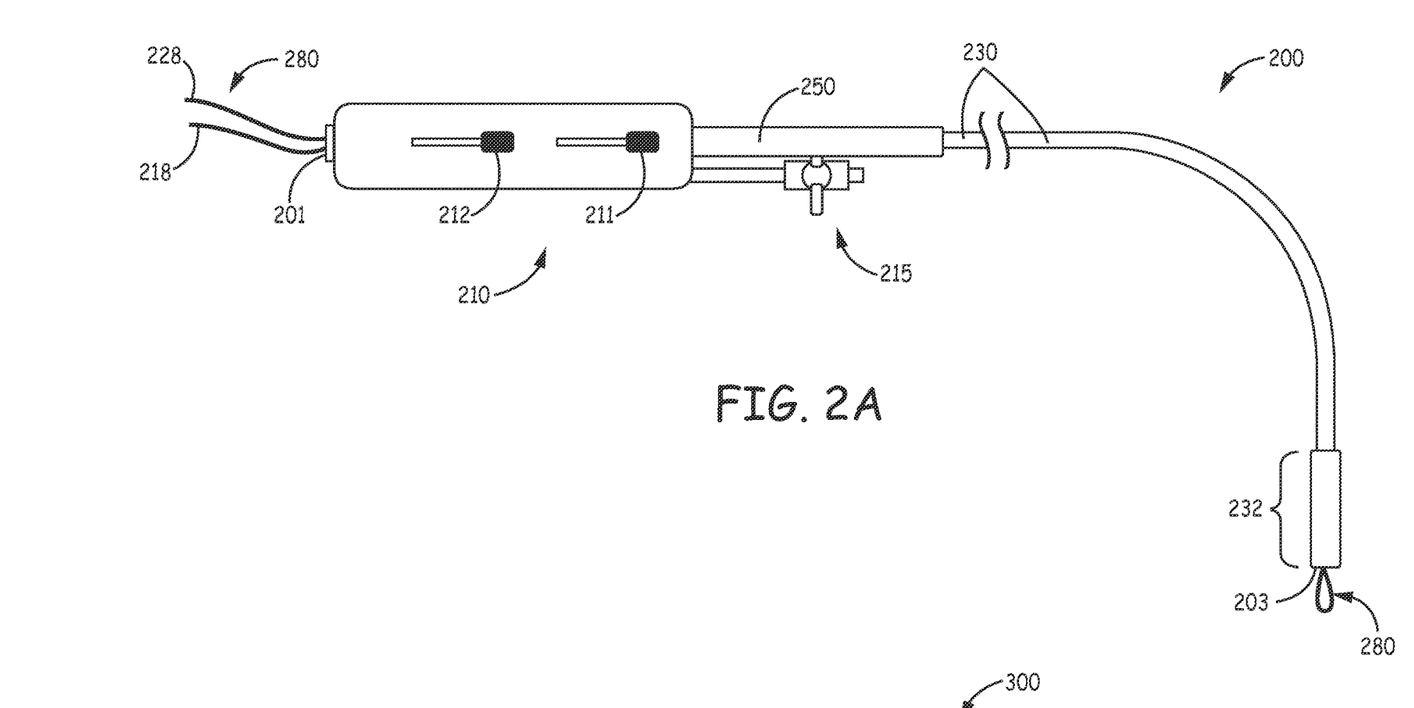
FIGS. 2A-B are plan views of an exemplary delivery catheter, which may be used to deploy embodiments of implantable medical devices disclosed herein.
Figure 2B:
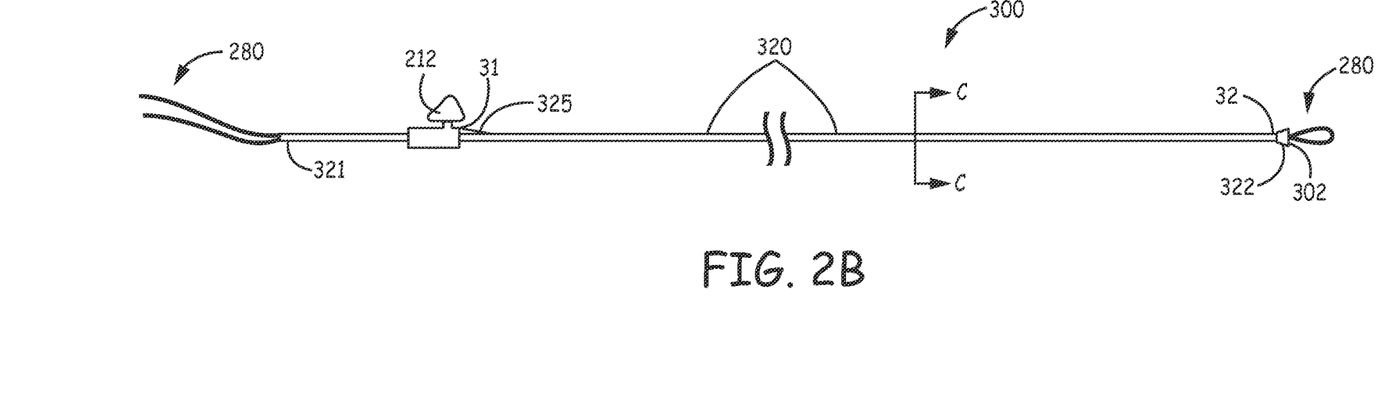

FIGS. 2A-B are plan views of the aforementioned exemplary delivery catheter 200, which may be used to deploy embodiments of implantable medical devices disclosed herein. FIG. 2A illustrates catheter 200 including a handle 210, an outer tube 230, a stabilizing sheath 250 being secured to handle 210 and surrounding a proximal portion of tube 230, in proximity to handle 210, and a flushing assembly 215 coupled to handle 210. FIG. 2A further illustrates a distal end 232 of outer tube 230 defining a distal opening 203 of tube 230, and, as will be described in greater detail below, distal end 232 is sized to contain an implantable medical device for deployment thereof. According to the illustrated embodiment, outer tube 230 is slideably engaged around a shaft 320 (shown in FIG. 2B, separate from a remainder of catheter 200), and is coupled to a control member 211 of handle 210, which is operable to retract and advance tube 230 relative to shaft 320. FIG. 2B illustrates shaft 320 extending between a proximal end 321 thereof and an enlarged distal-most end 322 thereof, wherein end 322 forms a distal opening 302 of shaft 320 and is configured to engage an implantable medical device that is contained in distal end 232 of outer tube 230.

Figure 9:
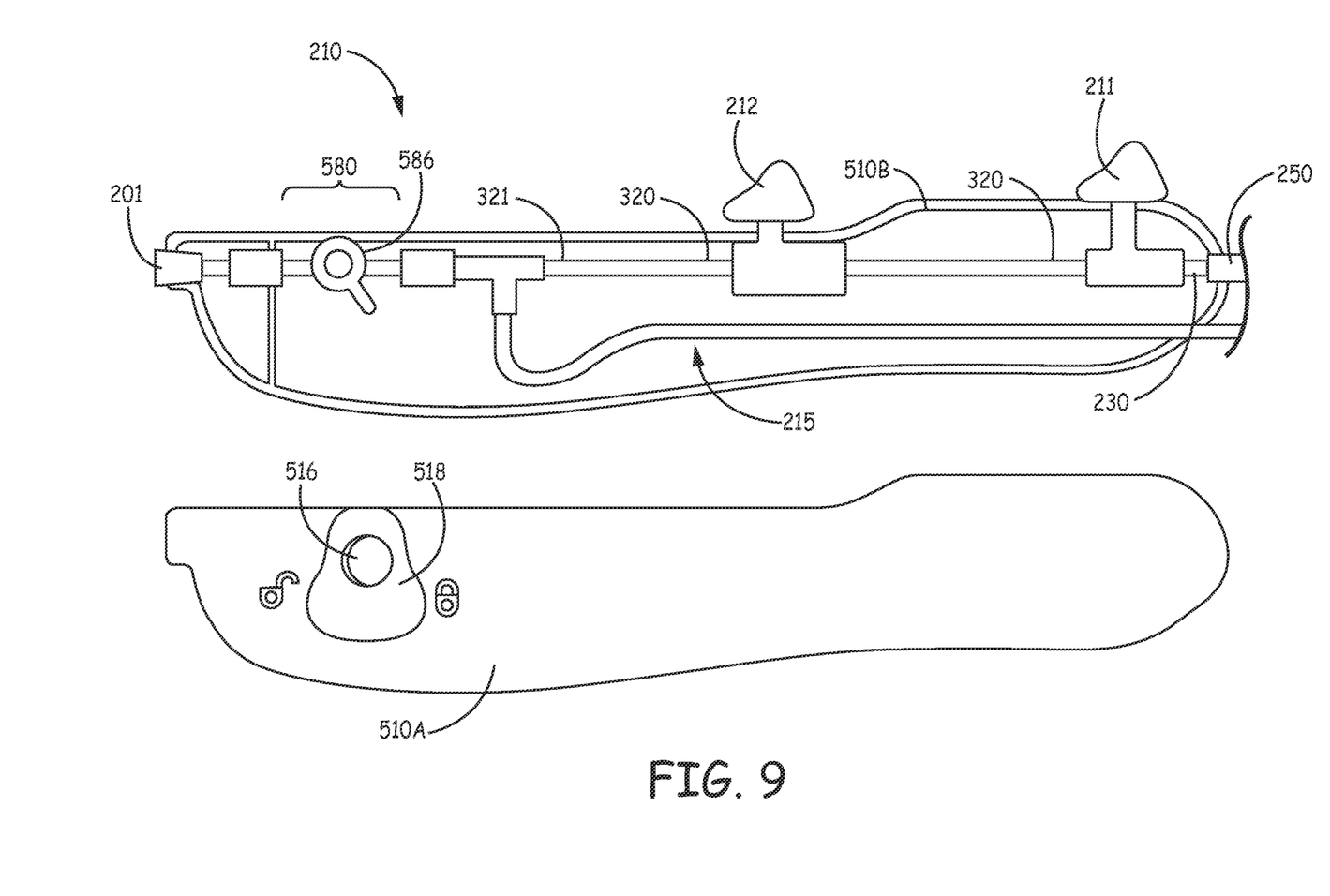
FIG. 9 is a plan view showing an internal configuration of a handle of the exemplary delivery catheter of FIGS. 2A-B.

According to FIGS. 2A-B, tether 280 of delivery catheter extends within shaft 320 such that opposing first and second ends 218, 228 thereof extend proximally from proximal end 321 of shaft 320 and out from a proximal port 201 of handle 210, while a looped portion thereof protrudes out from distal opening 302 of shaft 320 and out from a distal opening 203 of outer tube 230. First and second ends 218, 228 of tether 280 preferably extend within separate lumens of shaft 320, for example, as can be seen in the cross-section view of FIG. 2C (along section line C-C of FIG. 2B). According to FIG. 2C, shaft 320 is formed, at least in part, by a multi-lumen tube 340, which may be extruded polyether block amide, polyurethane, or silicone rubber, or a composite thereof, and may include an overlay (not shown), for example, formed of braid-reinforced polyether block amide. According to the illustrated embodiment, multi-lumen tube 340 includes one, relatively large lumen 341, and three, relatively small lumens 342-344, wherein lumens 341-343 are in fluid communication with distal opening 302 of shaft 320 and with proximal port 201 of handle 210, and wherein ends 218, 228 of tether 280 extend within lumens 342, 343. With reference to FIG. 9, which will be described in greater detail below, proximal end 321 of shaft 320 is shown secured within handle 210 so that lumens 341-343 are also in fluid communication with flushing assembly 215.

Figure 2C:
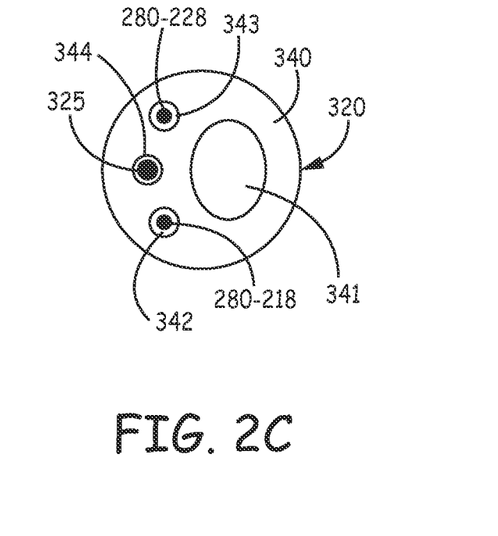
FIG. 2C is a cross-section view through section line C-C of FIG. 2B.

FIG. 2B-C further illustrate shaft 320 having a pull wire 325 extending within lumen 344, wherein a proximal end 31 thereof is coupled to a second control member 212 of handle 210, and a distal end thereof is anchored at a location 32, which is in proximity to distal-most end 322. According to the illustrated embodiment, movement of second control member 212, actuates pull wire 224 to bend shaft 320 and outer tube 230, for example, to facilitate maneuvering delivery catheter 200 up through the inferior vena cava IVC and into the right ventricle RV from the right atrium RA, as shown in FIG. 1. Some methods of use and construction details for exemplary delivery catheter 200 are described in a commonly assigned United States Patent Application, which has the Ser. No. 14/039,937.

Figure 3A:
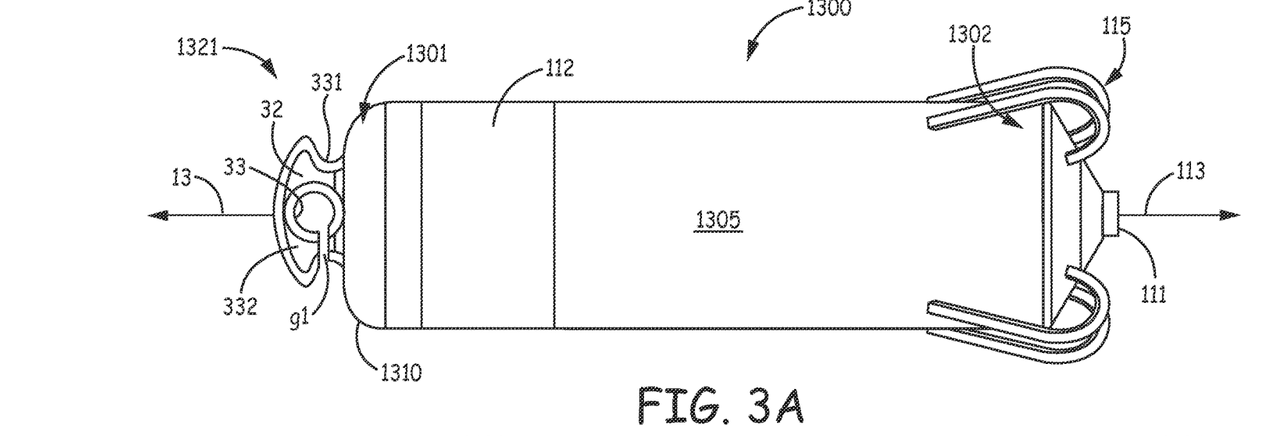
FIG. 3A is a plan view of a relatively compact implantable medical device of a first type, according to some embodiments of the present invention.

FIG. 3A is a plan view of a relatively compact implantable medical device 1300 of a first type, according to some embodiments, which may be deployed by delivery catheter 200. FIG. 3A illustrates device 1300 including a hermetically sealed housing 1305, for example, formed from a biocompatible and biostable metal such as titanium, and an electrode 111 and a fixation member 115, both mounted in proximity to a distal end 1302 of housing 1305. Housing 1305 is shown extending along a longitudinal axis 13, between a proximal end 1301 thereof and distal end 1302. Device 1300 further includes an electronic controller (not shown), for example, a pulse generator and an associated power supply, contained in housing 1305, wherein electrode 111 is electrically coupled to the controller via a hermetically sealed feedthrough assembly (not shown) such as is known in the art. Housing 1305 may be overlaid with an insulative layer, for example, medical grade polyurethane, parylene, or silicone, and another electrode 112 may be formed by removing a portion of the insulative layer to expose the metallic surface of housing 1305. Electrodes 111, 112 may function together for bipolar pacing and sensing, when device 1300 is deployed and fixation member 115 secures electrode 111 in intimate tissue contact at a target implant site. FIG. 2A further illustrates device 1300 including a tether catch 1321 for engaging a tether, for example, tether 280 of delivery catheter 200, wherein tether catch 1321 is formed by a relatively rigid structure 32 that protrudes from proximal end 1301 of housing 1305 and includes a hook surface 33 that extends between a first end 331 of structure 32 and a second end 332 of structure 32. According to the illustrated embodiment, second end 332 of structure 32 is spaced apart from proximal end 1301 of housing 1305 by a gap g1 of a size no greater than a thickness of tether 280.

Figure 3B:
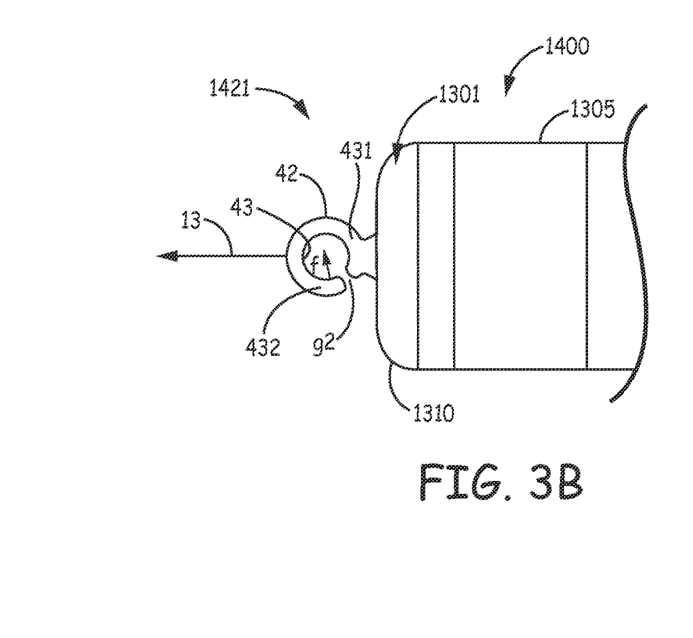
FIGS. 3B-C are partial plan views some alternate embodiments of the first type of medical device.
Figure 3C:
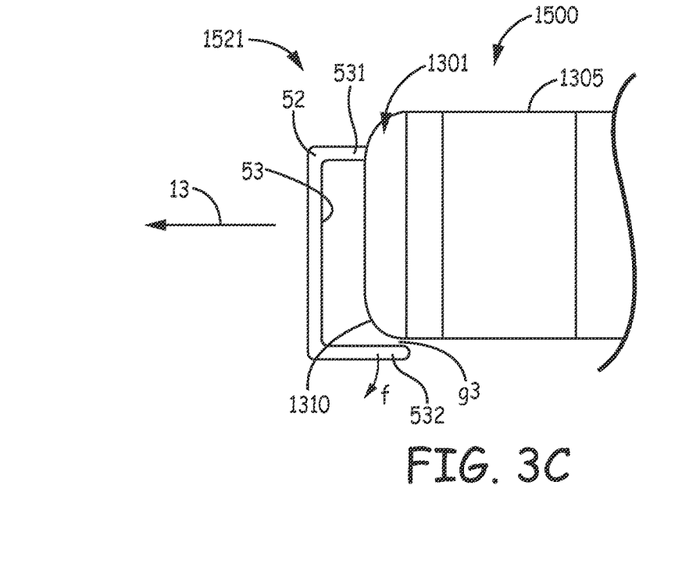

FIGS. 3B-C are partial plan views of additional devices 1400 and 1500 of the first type, each of which includes an alternative embodiment tether catch 1421 and 1521, respectively. Tether catches 1421, 1521, like catch 1321, are each formed by a rigid structure 42, 52, respectively, that protrudes from proximal end 1301 of housing 1305. FIGS. 3B-C illustrate each tether catch 1421, 1521 including a hook surface 43, 53, which, like hook surface 33 of catch 1321, extends between a corresponding first end 431, 531 and a second end 432, 532 of structure 42, 52. Yet, structures 42, 52 and respective hook surfaces 43, 53 are configured so that gaps g2 and g3, which are between respective second ends 432, 532 and proximal end 1301, are oriented and positioned relative to proximal end 1301 differently from one another, and differently from that of tether catch 1321. Gaps g2, g3, like gap g1, are of a size no greater than the thickness of tether 280, and, according to some embodiments, the size of one or both is less than the thickness of tether, wherein second ends 432, 532 are moveable from the illustrated position to a second position, for example, per arrow f, to enlarge gaps g2, g3 to a size that approaches a thickness of tether 280. According to some exemplary embodiments, structure 32, 42, 52 of each tether catch 1321, 1421, 1521 is formed from a relatively rigid biocompatible and biostable material such as titanium, stainless steel or even a hard plastic, wherein structures 42, 52, may have an inherent elasticity that allows for the aforementioned movement of second ends 432, 532, per arrow f. With further reference to FIGS. 3A-C, gaps g1, g2 are recessed toward longitudinal axis 13 from a shoulder 1310 of housing 1305, whereas gap g3 extends alongside shoulder 1310. In any case, gaps g1, g2, g3 allow for passage of tether 280 therethrough and into the perimeter of the corresponding hooked surface 33, 43, 53, for example, when tether 280 is tensioned according to methods described below. Then, once the looped portion of tether 280 comes into the perimeter of hooked surface 33, 43, 53, it may bear against a portion of hook surface 33, 43, 53 that faces directly toward proximal end 1301 of device housing 1305.

Figure 4:
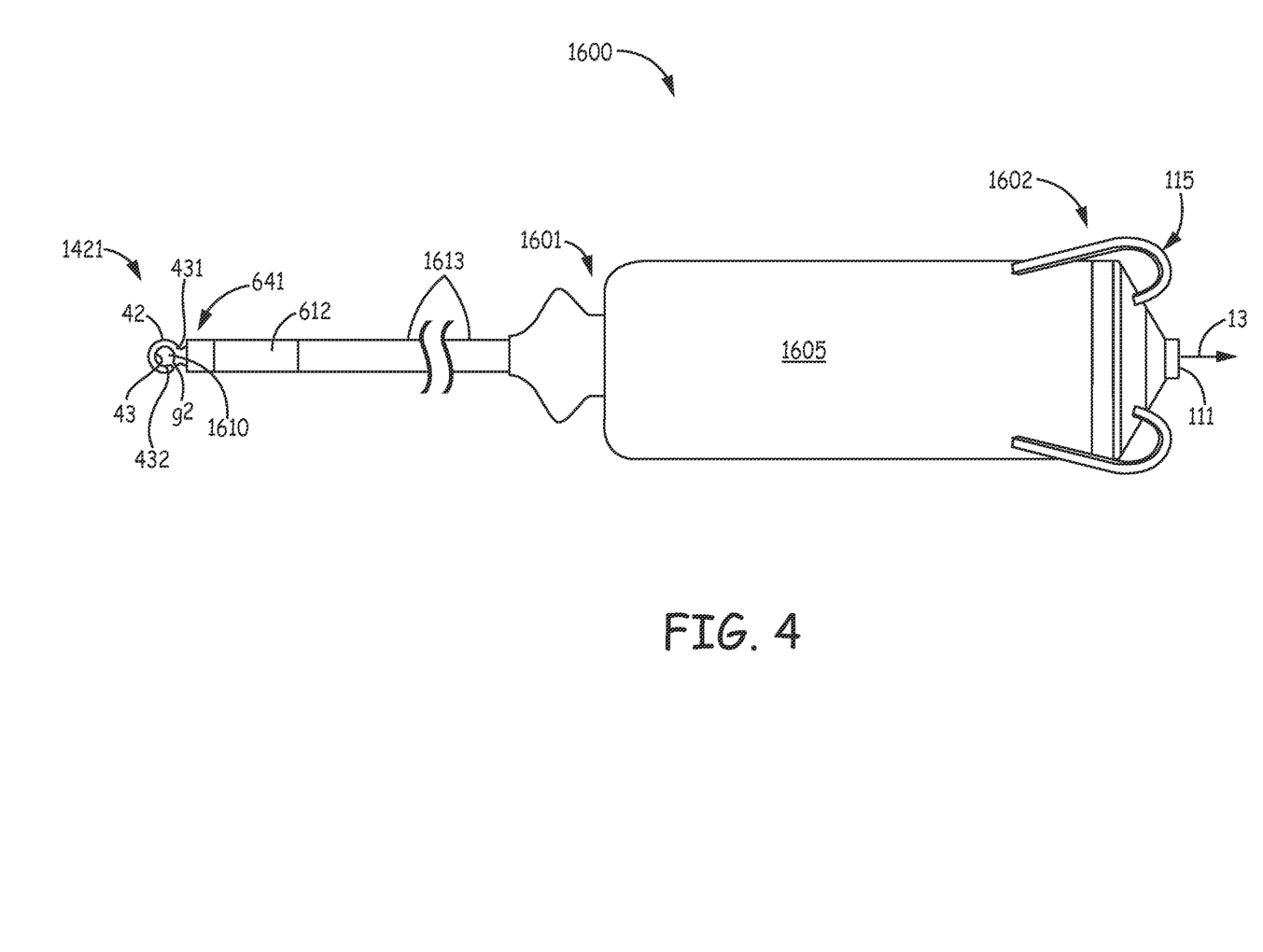
FIG. 4 is a plan view of a relatively compact implantable medical device of a second type, according to some embodiments.

FIG. 4 is a plan view of a relatively compact implantable medical device 1600 of a second type which includes a flexible extension 1613, according to some embodiments. FIG. 4 illustrates device 1600 including a hermetically sealed housing 1605, cardiac pacing and sensing electrodes 111, 612, and fixation member 115 coupled to a distal end 1602 of device housing 1605. Like the above-described housing 1305 of the first type of devices shown in FIGS. 3A-C, housing 1605 contains an electronic controller that is coupled to electrode 111 via an hermetically sealed feedthrough assembly known in the art. Unlike the first type of devices, device 1600 includes a flexible extension 1613 on which sense electrode 612 is mounted in proximity to a free end 641 thereof, wherein extension 1613 may be formed by an insulated conductor that electrically couples electrode 612 to the electronic controller contained in device housing 1605. According to the illustrated embodiment, flexible extension 1613 extends proximally from a proximal end 1601 of housing 1605, such that sense electrode 612 is spaced a distance from proximal end 1605, for example, to be located for atrial sensing (P-waves) when device 1600 is implanted in the right ventricle RV (FIG. 1). FIG. 4 further illustrates device 1600 including tether catch 1421, which protrudes from free end 641 of flexible extension 1613, and which is oriented so that a portion hook surface 43 faces directly toward free end 641 of extension 1613, and whose gap g1 is recessed from a shoulder 1610 of free end 641.

The configuration of any of the above described tether catches 1321, 1421, 1521 increases the ease by which the operator may load corresponding device 1300, 1400, 1500, 1600 into a delivery catheter (e.g., delivery catheter 200 with tether 280), for example, just prior to gaining venous access to a patient for the deployment of the device, and according to methods described below in conjunction with FIGS. 5A-9.

Figure 5A:
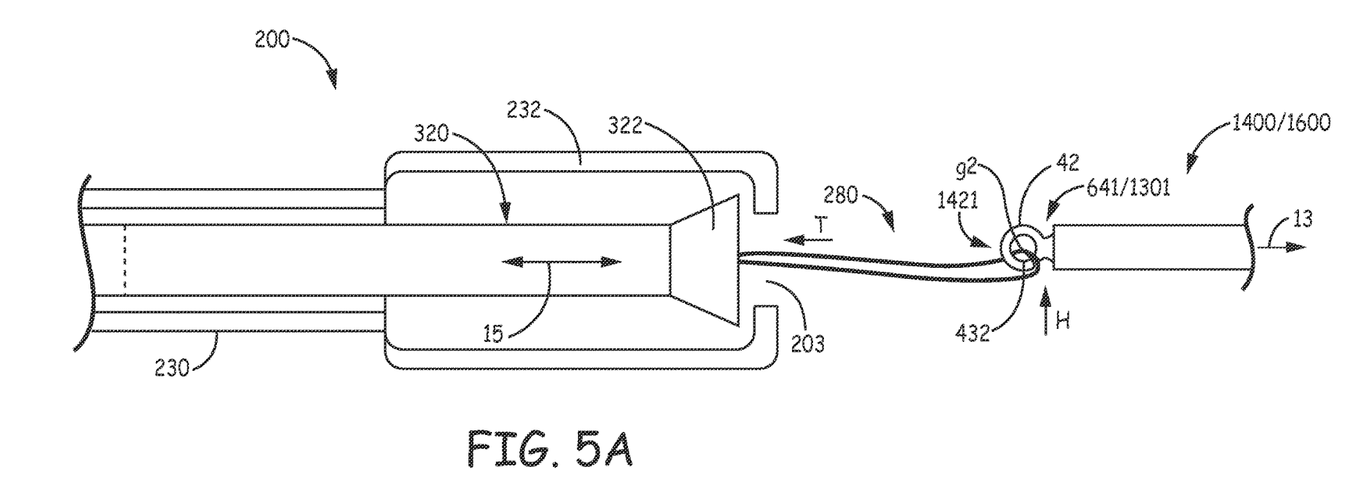
FIGS. 5A-B are schematics depicting initial loading steps, according to some methods of the present invention.
Figure 5B:
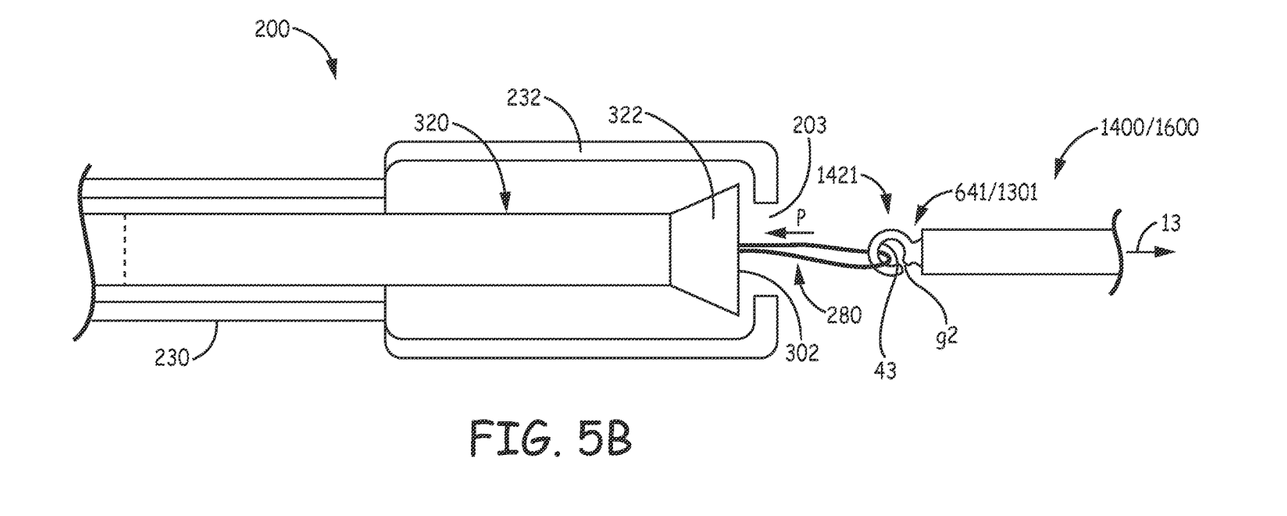

FIGS. 5A-B are schematics depicting initial steps for loading either device 1400 of the first type, or device 1600 of the second type, according to some methods of the present invention. FIG. 5A illustrates the looped portion of tether 280, which protrudes out from distal opening 203 of catheter 200, being positioned in close proximity to gap g2 of tether catch 1421. While holding the positioned tether 280 against gap g2, per arrow H, the operator can create tension in tether 280, per arrow T, to bring the looped portion through gap g2 and into the perimeter of hooked surface 43 so that tether catch 1421 engages tether 280, for example, as shown in FIG. 5B. If gap g2 is smaller than a thickness of tether 280, second end 432 may flex, or move inward (per arrow f of FIG. 3B) in response to the tension in tether 280, alternately the thickness of tether 280 under the tension may be slightly compressed to pass through gap g2. Due to a relatively floppy nature of tether 280, which may be formed from a polyester fiber having a fluoropolymer coating, such as PTFE, and due to the size of gap g2, as described above, in conjunction with the position and orientation of gap g2, it is highly unlikely that the engaged tether 280 will slip out from the perimeter of hooked surface 43 when the tension is released. With reference back to FIG. 3C, the same can said for gap 3 of tether catch 1521 in regard to size, position and orientation thereof. Once engaged with tether catch 1421, the operator can pull tether 280, in a direction substantially parallel to longitudinal axis 13, per arrow P, for example, by grasping ends 218, 228 that protrude out from proximal port 201 of catheter 200 (FIG. 2A), so that the looped portion bears against that portion of hooked surface 43 which faces toward proximal end 1301 or free end 641. With reference back to FIG. 3C, it may be appreciated that a similar method may be used to engage tether 280 with tether catch 1521 of device 1500.

Figure 6A:
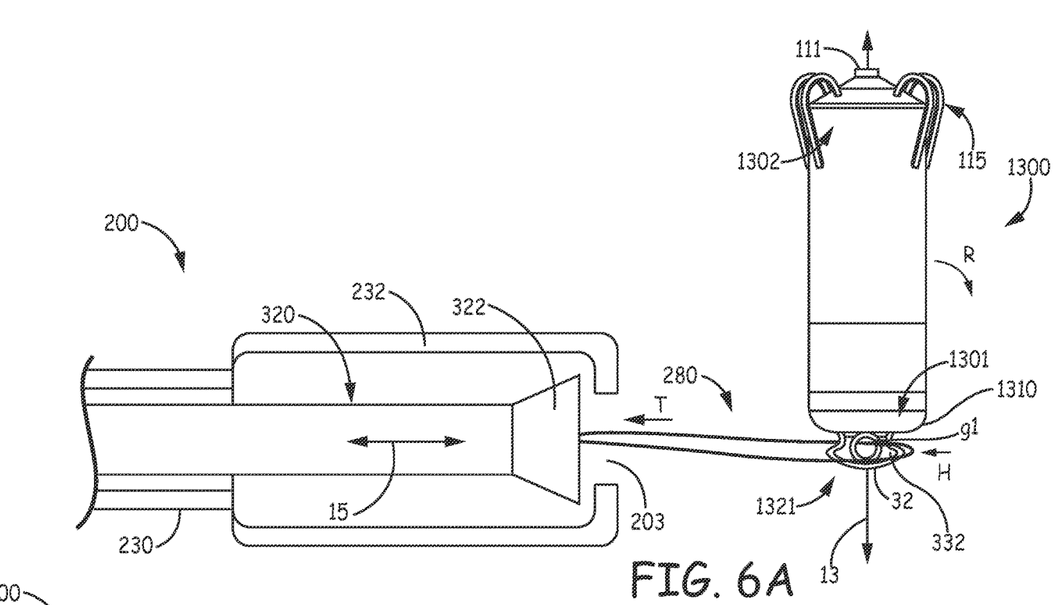
FIGS. 6A-B are schematics depicting initial loading steps, according to some alternate methods of the present invention.
Figure 6B:
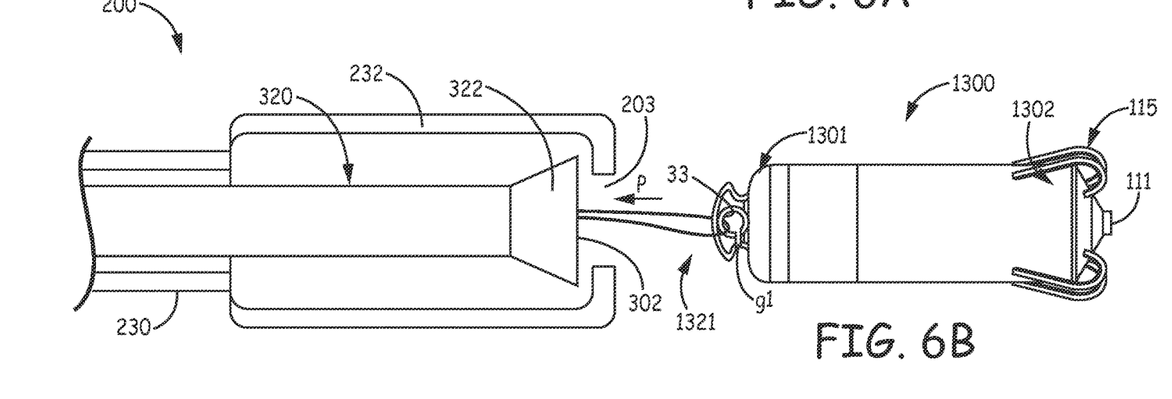

FIGS. 6A-6B are schematics depicting slightly different initial steps for loading device 1300 into delivery catheter 200. Due to the configuration of structure 32 that forms tether catch 132, gap g1 is recessed between second end 332 of structure 32 and shoulder 1310 of device housing 1305 and is oriented so that passage therethrough is approximately orthogonal to longitudinal axis 13. Thus, FIG. 6A illustrates device 1300 being initially oriented so that axis 13 is approximately orthogonal to a longitudinal axis 15 that extends along catheter shaft 320 in proximity to enlarged distal-most end 322. FIG. 6A further illustrates the looped portion of tether 280 being positioned in close proximity to gap g1 of tether catch 1321, so that when the operator holds the positioned tether 280 against gap g1, per arrow H, and creates tension in tether 280, per arrow T, the looped portion is brought through gap g1 and into the perimeter of hooked surface 33 for engagement with tether catch 1321. Once tether 280 is engaged, the operator rotates device 1300, per arrow R, to approximately align axes 13, 15, and then pulls tether 280, per arrow P, so that the looped portion bears against that portion of hooked surface 33 which faces toward proximal end 1301 of device housing 1305, as shown in FIG. 6B.

Figure 7:
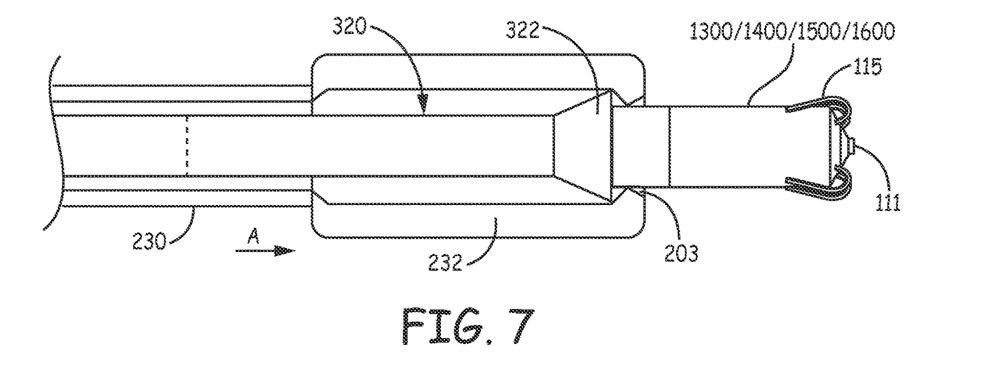
FIGS. 7-8 are schematics depicting subsequent loading steps, according to some embodiments.

Pulling tether 280, when engaged with any one of tether catches 1321, 1421, 1521 of devices 1300, 1400, 1500, 1600, so that the looped portion thereof bears against that portion of hooked surface 33, 43, 53 which faces toward proximal end 1301 or free end 641, brings proximal end 1301, 1601 of device housing 1305, 1605 into engagement with enlarged distal-most end 322 of catheter shaft 320, according to some loading methods, as shown in FIG. 7. In the case of device 1600 (FIG. 4A), shaft 320 includes a single lumen portion that extends between distal-most end 322 and a distal terminal end of the above-described multi-lumen tube 340 (FIG. 2C), which is designated with a dashed line of FIGS. 5A-B and 7; this single lumen portion is sized to accommodate flexible extension 1613 therein when housing proximal end 1601 is engaged with shaft distal-most end 322. A construction of a suitable assembly for such a shaft that accommodates flexible extension 1613 is described for a delivery system in a co-pending and commonly assigned United States Patent Application having the Ser. No. 14/548,958 (Attorney Docket No. C00008873.USU1).

Figure 8:
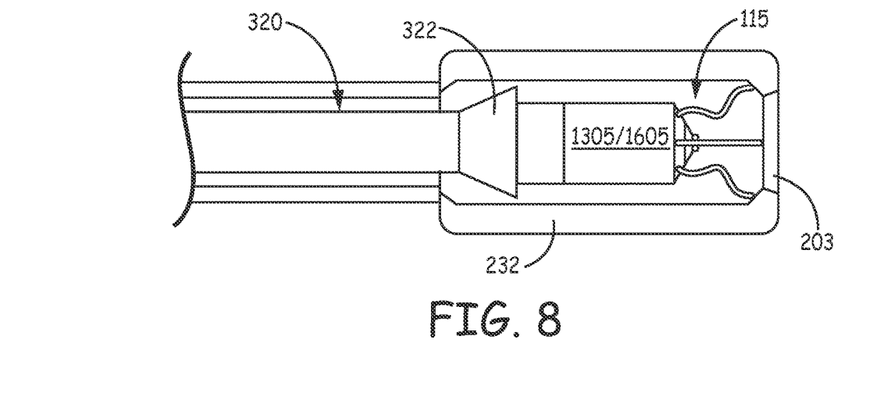

Subsequently, to complete the loading of any of devices 1300, 1400, 1500, 1600 into delivery catheter 200, the operator may advance, per arrow A, outer tube 230 of delivery catheter 200 relative to shaft 320, for example, via movement of control member 211 of handle 210 (FIG. 2A), until distal end 232 thereof encloses device housing 1305, 1605 and holds fingers of fixation member 115 in an extended position, as shown in FIG. 8. The fingers of fixation member 115 may be cut from Nitinol tubing, according to methods known in the art, and fixation member 115 may be mounted to distal end 1302, 1602 of device housing 1305, 1605 in a manner similar to that described for a fixation component 102 in co-pending and commonly assigned United States Patent Application 2012/0172690. The super-elastic nature of Nitinol allows the fingers to elastically deform between a relaxed condition, as shown in FIGS. 3A and 4, and the extended condition shown in FIG. 8, wherein the extended condition allows for initial engagement of the fingers with tissue, when distal opening 203 is located in close proximity to an implant site and outer tube 230 is retracted to deploy device 200 at the implant site.

According to some methods, prior to advancing outer tube 230 to complete the loading, the operator may secure a proximal portion of tether 280 within handle 210 of delivery catheter 200, for example, with a tether engaging conduit 580 of handle 210, which can be seen in FIG. 9. FIG. 9 is a plan view of an internal configuration of handle 210 wherein a first portion of an outer surface, or shell 510A of handle 210 is removed to see an arrangement of components within a second portion of the shell 510B. FIG. 9 illustrates conduit 580 extending between proximal port 201 and proximal end 321 of shaft 320 and including a valve member 586 integrated therein. According to an exemplary embodiment, valve member 586 is constructed like a stop-cock valve known to those skilled in the art. FIG. 9 further illustrates first portion of shell 510A including an aperture 516, which is formed through a recessed surface 518 of portion 510A, and which provides access to valve member 586 so that an operator can move valve member 586 between an open position and a closed position. In the open position, valve member 586 allows free movement of tether 280 therethrough and fluid communication between proximal port 201 and lumens 341-343 (FIG. 2C) of shaft 320. In the closed position, valve member 586 secures, or clamps tether 280, while the operator advances outer tube 230 relative to shaft 320 to complete the loading of any of devices 1300, 1400, 1500, 1600, as described above, and also while the operator navigates and articulates delivery catheter 200, and then deploys the device.

In the foregoing detailed description, the invention has been described with reference to specific embodiments. However, it may be appreciated that various modifications and changes can be made without departing from the scope of the invention as set forth in the appended claims.

The invention claimed is:

1. An implantable medical device comprising:
   an electronic controller,
   a hermetically sealed housing containing the controller,
   an electrode electrically coupled to the controller and mounted in proximity to a distal end of the housing,
   a fixation member mounted to the distal end of the housing,
   a tether that defines an uncompressed cross-sectional width and a compressed cross-sectional width that is relatively smaller than the uncompressed cross-sectional width, the tether being looped within a delivery catheter, and
   a tether catch for engaging the tether, the tether catch being formed by a relatively rigid structure protruding from a proximal end of the housing, the housing extending along a longitudinal axis between the proximal and distal ends, and wherein the tether catch comprises:
      a hook surface extending between a first end and a second end of the relatively rigid structure that is configured to receive the tether, the hook surface including a portion facing directly toward the proximal end of the housing; and
      the second end of the structure being spaced apart from the proximal end of the housing by a gap that defines a distance no greater than the uncompressed cross-sectional width when the structure is in a resting state.

2. The device of claim 1, wherein the gap is recessed toward the longitudinal axis from a shoulder of the housing.

3. The device of claim 1, wherein the distance of the gap from the second end of the structure to the proximal end of the housing is less than the uncompressed cross-sectional width of the tether.

4. The device of claim 1, wherein the tether comprises polymeric materials and the structure is configured to define the gap such that the tether compresses to define the compressed cross-sectional width when the tether is within the gap as a result of the distance of the gap from the second end of the structure to the proximal end of the housing being no greater than the compressed cross-sectional width of the tether.

5. The device of claim 1, wherein the second end of the structure defines the gap at a fixed position relative to the proximal end of the housing such that the gap enables access to the portion of the hook surface facing directly toward the proximal end of the housing by the tether along an axis that is generally perpendicular to the longitudinal axis of the housing.

6. The device of claim 1, wherein:
   the structure in the resting state at least partially defines a hole with a substantially static cross-sectional shape, the hole configured to receive the tether; and
   the structure at least partially defines the hole with the substantially static cross-sectional shape as the structure receives the tether.

7. The device of claim 1, wherein the tether comprises a first end and a second end and a looped portion between the first end and the second end, wherein the looped portion protrudes from a distal end of the delivery catheter, and wherein the first end and the second end extend from the proximal end of the delivery catheter.

8. The device of claim 7 wherein the first end extends from a lumen of the delivery catheter and the second end extends from a separate lumen of the delivery catheter.

* * * * *